United States Patent
Hirata et al.

(10) Patent No.: US 12,296,467 B2
(45) Date of Patent: May 13, 2025

(54) BENDING STRUCTURAL BODY

(71) Applicant: NHK SPRING CO., LTD., Kanagawa (JP)

(72) Inventors: Takafumi Hirata, Kanagawa (JP); Yuki Hotoda, Kanagawa (JP); Masahiro Inaba, Kanagawa (JP); Yuki Hayakawa, Kanagawa (JP)

(73) Assignee: NHK SPRING CO., LTD., Kanagawa (JP)

( * ) Notice: Subject to any disclaimer, the term of this patent is extended or adjusted under 35 U.S.C. 154(b) by 89 days.

(21) Appl. No.: 18/034,047

(22) PCT Filed: Oct. 29, 2021

(86) PCT No.: PCT/JP2021/040036
§ 371 (c)(1),
(2) Date: Apr. 26, 2023

(87) PCT Pub. No.: WO2022/092268
PCT Pub. Date: May 5, 2022

(65) Prior Publication Data
US 2023/0330871 A1      Oct. 19, 2023

(30) Foreign Application Priority Data
Oct. 30, 2020   (JP) .................... 2020-183190

(51) Int. Cl.
*B25J 18/06*       (2006.01)
*B25J 9/10*        (2006.01)

(52) U.S. Cl.
CPC ............... *B25J 18/06* (2013.01); *B25J 9/104* (2013.01)

(58) Field of Classification Search
CPC .................................. B25J 9/104; B25J 18/06
(Continued)

(56) References Cited

U.S. PATENT DOCUMENTS

| | | | |
|---|---|---|---|
| 5,154,705 A | | 10/1992 | Fleischhacker et al. |
| 5,271,543 A | * | 12/1993 | Grant .................. A61B 17/115 |
| | | | 227/19 |

(Continued)

FOREIGN PATENT DOCUMENTS

| | | | | |
|---|---|---|---|---|
| CN | 101394975 A | * | 3/2009 | .............. B25J 18/06 |
| JP | H1170488 | | 3/1999 | |

(Continued)

OTHER PUBLICATIONS

"International Search Report (Form PCT/ISA/210) of PCT/JP2021/040036", mailed on Jan. 11, 2022, with English translation thereof, pp. 1-4.

(Continued)

*Primary Examiner* — Bobby Rushing, Jr.
(74) *Attorney, Agent, or Firm* — JCIPRNET

(57) ABSTRACT

The bending structural body comprises: an inner cylinder that is formed from a first inner coil part and a first outer coil part, and in which wound parts corresponding to the first inner coil part are respectively fitted to pitches between adjacent wound parts of the first outer coil part; an outer cylinder that covers at least some of the outer circumference of the inner cylinder with a space therebetween, that is formed from a second inner coil part and a second outer coil part, and in which wound parts corresponding to the second inner coil part are respectively fitted to pitches between adjacent wound parts of the second outer coil part; and drive wires and guide wires that are guided and axially inserted into the space between the inner cylinder and the outer cylinder.

9 Claims, 6 Drawing Sheets

(58) Field of Classification Search
USPC .......................................... 494/448; 600/140
See application file for complete search history.

(56) References Cited

U.S. PATENT DOCUMENTS

| | | | | |
|---|---|---|---|---|
| 5,405,073 | A * | 4/1995 | Porter | A61B 17/072 227/19 |
| 5,465,894 | A * | 11/1995 | Clark | A61B 17/072 227/19 |
| 5,851,212 | A * | 12/1998 | Zirps | A61B 34/71 606/174 |
| 5,873,866 | A * | 2/1999 | Kondo | F16L 11/088 604/526 |
| 7,422,559 | B2 * | 9/2008 | Kehoskie | G01N 21/954 600/156 |
| 2003/0229420 | A1 | 12/2003 | Buckingham et al. | |
| 2006/0111614 | A1 * | 5/2006 | Saadat | A61B 1/0008 600/129 |
| 2019/0145670 | A1 * | 5/2019 | Hofbauer | F25B 30/02 62/6 |
| 2021/0307773 | A1 * | 10/2021 | Hirata | A61B 17/2909 |

FOREIGN PATENT DOCUMENTS

| | | | |
|---|---|---|---|
| JP | 2009538186 | 11/2009 | |
| JP | 2020026019 | 2/2020 | |
| WO | 2015126752 | 8/2015 | |
| WO | WO-2020036085 A1 * | 2/2020 | ............. A61B 17/29 |

OTHER PUBLICATIONS

"Office Action of Taiwan Counterpart Application", issued on May 11, 2022, with English translation thereof, pp. 1-10.

"International Preliminary report on patentability (Form PCT/IB/326) mailed on May 11, 2023, International Preliminary report on patentability (Form PCT/IB/338) mailed on May 11, 2023, International Preliminary report on patentability (Form PCT/IB/373) issued on May 2, 2023, and Written Opinion of the International Searching Authority (Form PCT/ISA237 Box No. I, V) with English translation thereof mailed on Jan. 11, 2022, of PCT/JP2021/040036", pp. 1-9.

"Search Report of Europe Counterpart Application", issued on Apr. 2, 2024, p. 1-p. 9.

* cited by examiner

BENDING STRUCTURAL BODY

CROSS-REFERENCE TO RELATED APPLICATION

This application is a 371 application of the International PCT application serial no. PCT/JP2021/040036, filed on Oct. 29, 2021, which claims the priority benefits of Japan Patent Application No. 2020-183190, filed on Oct. 30, 2020. The entirety of each of the above-mentioned patent applications is hereby incorporated by reference herein and made a part of this specification.

TECHNICAL FIELD

The invention relates to a bending structural body provided for joint function parts such as robots and manipulators.

BACKGROUND TECHNOLOGY

Some robots, manipulators, or actuators have joint function parts that enable bending and extension. The bending structural body as shown in Patent Literature 1 is used as such a joint function part.

The bending structural body of Patent Literature 1 is configured by engaging a plurality of disk elements that are mutually swingable, and performs bending motion as a whole by swinging each disk element.

An actuation cable, which is a cord-like member, is inserted through and guided by each disk element. A bending operation of the bending structural body is performed by pulling the actuation cable.

However, the above-described conventional bending structural body has a complicated structure because the bending structural body connects a plurality of disk elements and inserts an actuation cable through each disk element.

CITATION LIST

Patent Literature

Patent Literature 1: Japanese Patent Publication No. 2009-538186

SUMMARY OF INVENTION

Technical Problem

The complicated structure of the bending structural body is the problem that needs to be solved.

Solution to Problem

The invention provides a bending structural body, including: an inner cylinder which includes a first inner coil part and a first outer coil part, and in which wound parts corresponding to the first inner coil part are fitted to spaces between adjacent wound parts of the first outer coil part; an outer cylinder which covers at least part of an outer circumference of the inner cylinder with a space therebetween and includes a second inner coil part and a second outer coil part, and in which wound parts corresponding to the second inner coil part are fitted to spaces between adjacent wound parts of the second outer coil part; and a plurality of cord-like members in a circumferential direction which are inserted into and guided by the space between the inner cylinder and the outer cylinder in an axial direction.

Effects of Invention

According to the invention, the bending structural body capable of bending and restoring is able to be realized with a simple structure simply by arranging a cord-like member used for manipulation or the like in the space between the inner cylinder and the outer cylinder composed of the inner and outer coil parts. Moreover, it is possible to stabilize the posture by preventing the compression of the inner cylinder and the outer cylinder before and after bending, and reliably guide the cord-like member through the space between the inner cylinder and the outer cylinder.

DESCRIPTION OF EMBODIMENTS

Figure 1:
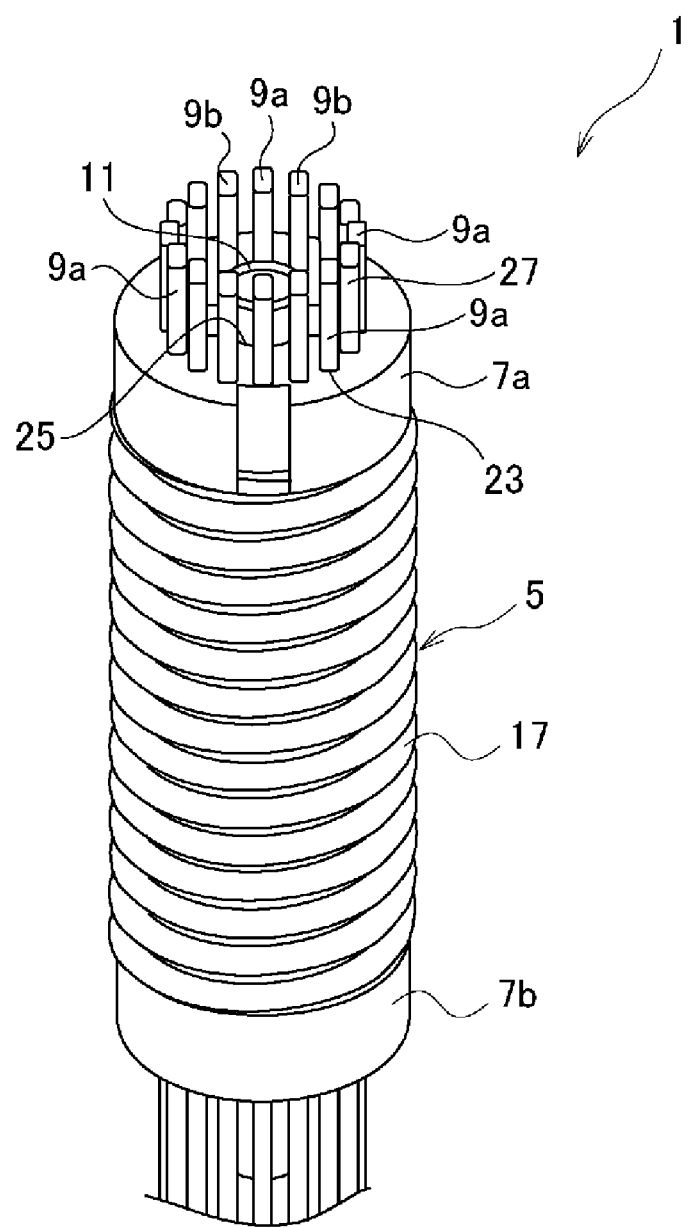
FIG. 1 is a perspective view showing the bending structural body according to Example 1 of the invention.

The purpose of simplifying the structure of the bending structural body was achieved by arranging the cord-like member in the space between the inner cylinder and the outer cylinder composed of the inner and outer coil parts.

That is, a bending structural body (1) includes an inner cylinder (3), an outer cylinder (5), and cord-like members (9a, 9b). The inner cylinder (3) includes a first inner coil part (15) and a first outer coil part (13), and the corresponding wound parts (15a) of the first inner coil part (15) are fitted to the spaces (13b) between the adjacent wound parts (13a) of the first outer coil part (13). The outer cylinder (5) covers at least part of the outer circumference of the inner cylinder (3) with the space (21) and includes a second inner coil part (19) and a second outer coil part (17), and the corresponding wound parts (19a) of the second inner coil part (19) are fitted to the spaces (17b) between the adjacent wound parts (17a) of the second outer coil part (17). The cord-like members (9a, 9b) are inserted into and guided by the space (21) between the inner cylinder (3) and the outer cylinder (5) in the axial direction.

The bending structural body (1) may include edge members (7a, 7b) that are attached to both ends of either one or both of the outer cylinder (5) and the inner cylinder (3) for inserting the cord-like members (9a, 9b) into the first insertion holes (23).

In addition, the bending structural body (1) may include a flexible member (11) inserted through the first inner coil part (15) of the inner cylinder (3), and the edge members (7a, 7b) may each have the second insertion hole (25) for inserting the flexible member (11).

The cord-like members (9a, 9b) include a drive cord-like member (9a) for driving one edge member (7a) with respect to the other edge member (7b), and a guide cord-like member (9b) provided on both sides of the drive cord-like member (9a) in the circumferential direction to limit the path of the drive cord-like member (9a).

Either one or both of the drive cord-like member (9a) and the guide cord-like member (9b) may be used as current-carrying paths.

Further, in the bending structural body (1), the first inner and outer coil parts (15, 13) of the inner cylinder (3) and the second inner and outer coil parts (19, 17) of the outer cylinder (5) may be reversely wounded to each other.

Example 1

[Bending Structural Body]

Figure 2:
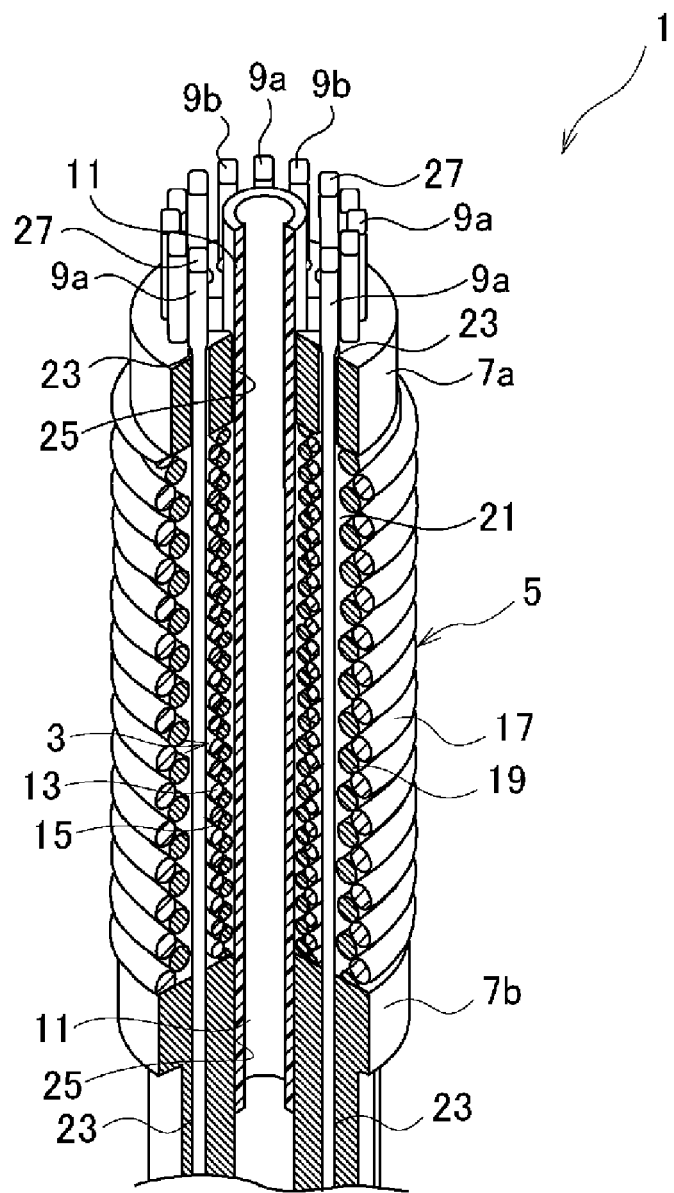
FIG. 2 is a perspective cross-sectional view of a part of the bending structural body of FIG. 1.
Figure 3:
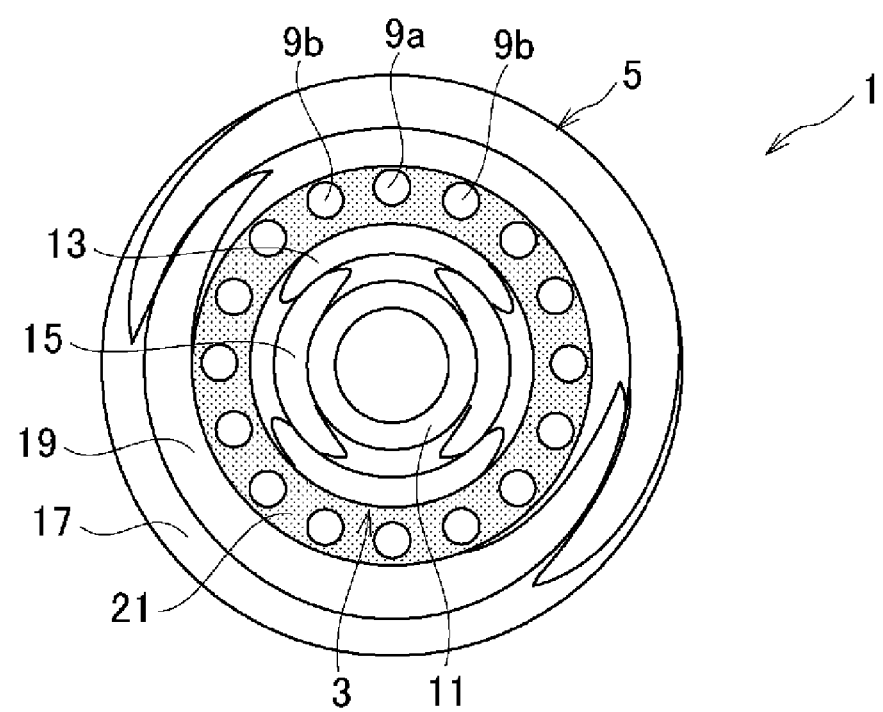
FIG. 3 is a plan view of the bending structural body of FIG. 1 with the edge member omitted.
Figure 4:
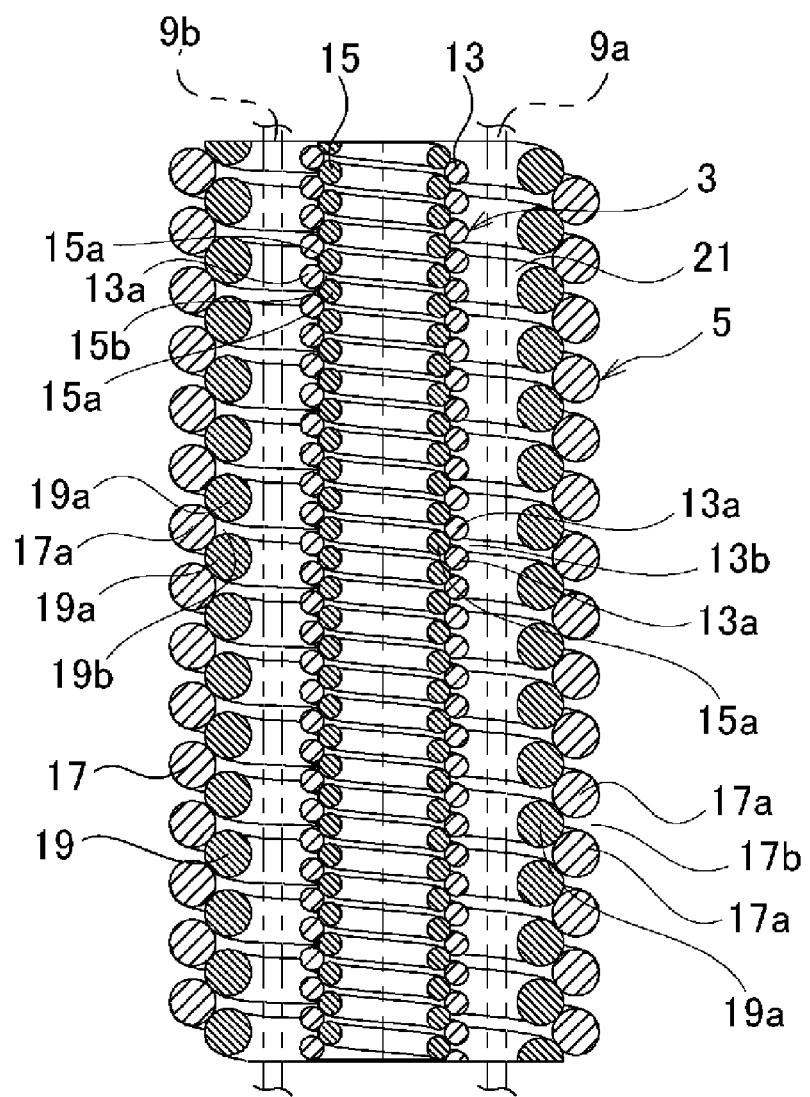
FIG. 4 is a cross-sectional view showing the inner cylinder and the outer cylinder of the bending structural body of FIG. 1.

FIG. 1 is a perspective view showing the bending structural body according to Example 1 of the invention. FIG. 2 is a perspective cross-sectional view of the same part. FIG. 3 is a plan view of the bending structural body with the edge member omitted. FIG. 4 is a cross-sectional view showing the inner cylinder and the outer cylinder of the bending structural body.

The bending structural body 1 of this example is applied to the joint function parts of various devices such as manipulators, robots, actuators, and the like for medical and industrial purposes, and is capable of relatively displacing device-side members coupled to both sides by bending and stretching operations.

This bending structural body 1 includes an inner cylinder 3, an outer cylinder 5, edge members 7a and 7b, drive wires 9a and guide wires 9b as cord-like members, and a flexible tube 11 as a flexible member.

The inner cylinder 3 is a double coil that is able to be elastically bent and restored in the axial direction, and includes a first outer coil part 13 and a first inner coil part 15.

The first outer coil part 13 and the first inner coil part 15 each include a coil spring having elasticity. Materials for the first outer coil part 13 and the first inner coil part 15 may both be metal, resin, or the like. Also, the cross-sectional shapes of the wires of the first outer coil part 13 and the first inner coil part 15 are circular. However, the cross-sectional shape is not necessarily circular, and may be semicircular, elliptic, or the like. Also, the cross-sectional shapes, wire diameters, materials, or the like of the first inner and outer coil parts 13 and 15 may be different from each other.

The first inner coil part 15 has a smaller center diameter than the first outer coil part 13 and is screwed into the first outer coil part 13. The center diameters of the first outer coil part 13 and the first inner coil part 15 are constant from one axial end to the other axial end. However, the center diameter of this first outer coil part 13 may also be changed in the axial direction.

The first outer coil part 13 has a plurality of pitches 13b as spaces separating axially adjacent wound parts 13a (between adjacent wound parts 13a) in the axial direction. The corresponding wound parts 15a of the first inner coil part 15 are fitted to the plurality of pitches 13b from inside. Due to this fitting, the wound part 15a of the first inner coil part 15 comes into contact with both of the adjacent wound parts 13a of the first outer coil part 13.

On the other hand, the first inner coil part 15 has a plurality of pitches 15b as spaces separating axially adjacent wound parts 15a (between adjacent wound parts 15a) in the axial direction. The corresponding wound parts 13a of the first outer coil part 13 are fitted to the plurality of pitches 15b from outside. Due to this fitting, the wound part 13a of the first outer coil part 13 comes into contact with both of the adjacent wound parts 15a of the first inner coil part 15.

Therefore, the inner cylinder 3 is restricted from being compressed in the axial direction.

The outer cylinder 5, like the inner cylinder 3, is a double coil that is able to be elastically bent and restored in the axial direction, and includes a second outer coil part 17 and a second inner coil part 19. This outer cylinder 5 covers the outer circumference of the inner cylinder 3 with a space 21 therebetween. When the outer cylinder 5 is shorter than the inner cylinder 3, the outer cylinder partially covers the inner cylinder 3 in the axial direction. Therefore, the outer cylinder 5 may be configured to cover at least part of the outer circumference of the inner cylinder 3 with the space 21 therebetween.

The space 21 is defined between the second inner coil part 19 of the outer cylinder 5 and the first outer coil part 13 of the inner cylinder 3 in the radial direction. The radial dimension of the space 21 is set slightly larger than the wire diameters of the drive wires 9a and the guide wires 9b.

Thereby, the inner cylinder 3 and the outer cylinder 5 serve as guides for the drive wires 9a and the guide wires 9b. The radial dimension of the space 21 may be appropriately set within a range that ensures the function of guiding the drive wires 9a and the guide wires 9b.

The second outer coil part 17 and the second inner coil part 19 of the outer cylinder 5 are configured similarly to the first outer coil part 13 and the first inner coil part 15 of the inner cylinder 3. However, the winding direction of the outer cylinder 5 may be the same as or reverse to the winding direction of the inner cylinder 3.

When the winding directions of the inner cylinder 3 and the outer cylinder 5 are reversed (reversely wound), the inner cylinder 3 and the outer cylinder 5 are able to resist torsion in reverse directions, and the torsional rigidity of the bending structural body 1 as a whole is able to be improved.

Like the first outer coil part 13 and the first inner coil part 15 of the inner cylinder 3, the second outer coil part 17 and the second inner coil part 19 include elastic coil springs and may be made of metal, resin, or the like. The cross-sectional shapes of the wires of the second outer coil part 17 and the second inner coil part 19 are circular, but not necessarily circular. Further, the cross-sectional shapes, materials, wire diameters, or the like of the second inner and outer coil parts 19 and 17 may be different from each other.

The second inner coil part 19 has a smaller center diameter than the second outer coil part 17 and is screwed into the second outer coil part 17. The center diameters of the second outer coil part 17 and the second inner coil part 19 are constant from one axial end to the other axial end, but may be changed in the axial direction.

The second outer coil part 17 has a plurality of pitches 17b separating axially adjacent wound parts 17a (between adjacent wound parts 17a) in the axial direction. The corresponding wound parts 19a of the second inner coil part 19 are fitted to the plurality of pitches 17b from inside. Due to this fitting, the wound part 19a of the second inner coil part 19 comes into contact with both of the adjacent wound parts 17a of the second outer coil part 17.

On the other hand, the second inner coil part 19 has a plurality of pitches 19b as spaces separating axially adjacent wound parts 19a (between adjacent wound parts 19a) in the axial direction. The corresponding wound parts 17a of the second outer coil part 17 are fitted to the plurality of pitches 19b from outside. Due to this fitting, the wound part 17a of the second outer coil part 17 comes into contact with both of the adjacent wound parts 19a of the second inner coil part 19.

Therefore, the outer cylinder 5 is restricted from being compressed in the axial direction.

The edge members 7a and 7b are cylindrical and made of metal or the like. Note that the edge members 7a and 7b may have other shapes such as a prism shape. These edge members 7a and 7b are respectively attached to the axial ends of the outer cylinder 5 by an appropriate fixing method such as welding. Also, the edge members 7a and 7b may be attached to the axial ends of the inner cylinder 3, or may be attached to the axial ends of both the inner cylinder 3 and the outer cylinder 5.

Attachment of the edge members 7a and 7b to the outer cylinder 5 is performed on either one of the second inner and outer coil parts 19 and 17. In this example, the edge members 7a and 7b are attached to the second outer coil part 17.

The first insertion hole 23 and the second insertion hole 25 are provided through the edge members 7a and 7b in the axial direction. The first insertion hole 23 axially communicates with the space 21 between the inner and outer cylinders 3 and 5 for inserting the drive wires 9a and the guide wires 9b.

The second insertion hole 25 communicates with the interior of the inner cylinder 3 in the axial direction for inserting the flexible tube 11. The second insertion hole 25 of this example is provided at the axial center of the edge members 7a and 7b and has a circular cross section.

The edge members 7a and 7b are respectively attached to the device-side members that are relatively displaced via the bending structural body 1. For example, one edge member 7a is attached to the device-side member on the distal side, and the other edge member 7b is attached to the device-side member on the proximal side. These edge members 7a and 7b may be omitted. In that case, both ends of the outer cylinder 5 may be directly attached to the device-side members.

The drive wires 9a and the guide wires 9b are drive cord-like members and guide cord-like members made of metal or the like. The drive wires 9a and the guide wires 9b have flexibility to an extent that does not hinder the bending and restoration of the bending structural body 1.

The cross-sectional shapes of the drive wires 9a and the guide wires 9b may be circular similar to the first insertion hole 23, or may be a different shape such as an ellipse or a rectangle. The drive wires 9a and the guide wires 9b may be stranded wires, NiTi (nickel titanium) single wires, piano wires, articulated rods, chains, cords, strings, ropes, or the like as long as the drive wires 9a and the guide wires 9b are cord-like members.

The guide wires 9b are not limited to metal or the like, and may be made of resin. Further, the guide wires 9b may be column-shaped or rod-shaped members instead of cord-like members.

The drive wires 9a and the guide wires 9b are axially inserted through and guided by the space 21 between the inner and outer cylinders 3 and 5. In this example, a plurality of drive wires 9a and guide wires 9b are provided at predetermined intervals in the circumferential direction. In addition, the drive wires 9a may be guided in a spiral shape around the axis instead of being guided straight along the axial direction.

The ends 27 of the drive wires 9a and the guide wires 9b are inserted through the first insertion holes 23 of the edge members 7a and 7b and pulled to the outside. The ends 27 pulled out from one edge member 7a are prevented from coming off by end processing.

The drive wires 9a enable one edge member 7a to drive the other edge member 7b. That is, the drive wires 9a bend the bending structural body 1 by being pulled in the axial direction, and are connected directly or indirectly to an operating mechanism not shown to be operated in the axial direction.

In addition, the operation in the axial direction means moving the drive wires 9a forward and backward in the axial direction. The number of drive wires 9a may be appropriately set according to the bending motion of the bending structural body 1.

The guide wires 9b are provided on both sides in the circumferential direction of each drive wire 9a to limit the path of the drive wires 9a. The guide wires 9b regulate the displacement of the drive wires 9a in the circumferential direction. In this example, the guide wires 9b and the drive wires 9a restrict the mutual displacement in the circumferential direction, thereby limiting the path of the drive wires 9a.

The guide wires 9b may also function as the drive wires 9a. Also, the guide wires 9b may be omitted. Furthermore, one or both of the drive wires 9a and the guide wires 9b may be used as a current-carrying path. In addition, it is also possible to use the inner cylinder 3 as a current-carrying path.

The flexible tube 11 is a tubular member made of resin or the like, and is inserted through the first inner coil part 15 of the inner cylinder 3. This flexible tube 11 has flexibility to an extent that does not hinder the bending and restoration of the bending structural body 1. The ends of the flexible tube 11 are inserted through the second insertion holes 25 of the edge members 7a and 7b and pulled to the outside. Further, as a cord-like member, the flexible tube 11 may be provided for current-carrying only rather than for driving and for guiding.

The flexible tube 11 is fitted into the second insertion hole 25 at the end. As a result, the inner cylinder 3 is positioned via the flexible tube 11 with respect to the edge members 7a and 7b. One of the edge members 7a and 7b may be used as a reference for positioning. The outer cylinder 5 is attached and positioned to the edge members 7a and 7b.

Therefore, in this example, the space 21 which is positioned between the inner and outer cylinders 3 and 5 by the edge members 7a and 7b and through which the drive wires 9a and the guide wires 9b are inserted is defined accurately.

Inside the flexible tube 11, a driving member such as an air tube and a push-pull cable for driving an end effector or the like is inserted. It should be noted that the flexible tube 11 may be omitted and a driving member such as an air tube and a push-pull cable, or other flexible members may be used as the flexible member. The flexible member itself such as the flexible tube 11 and the driving member may be omitted.

[Motion]

Figure 5:
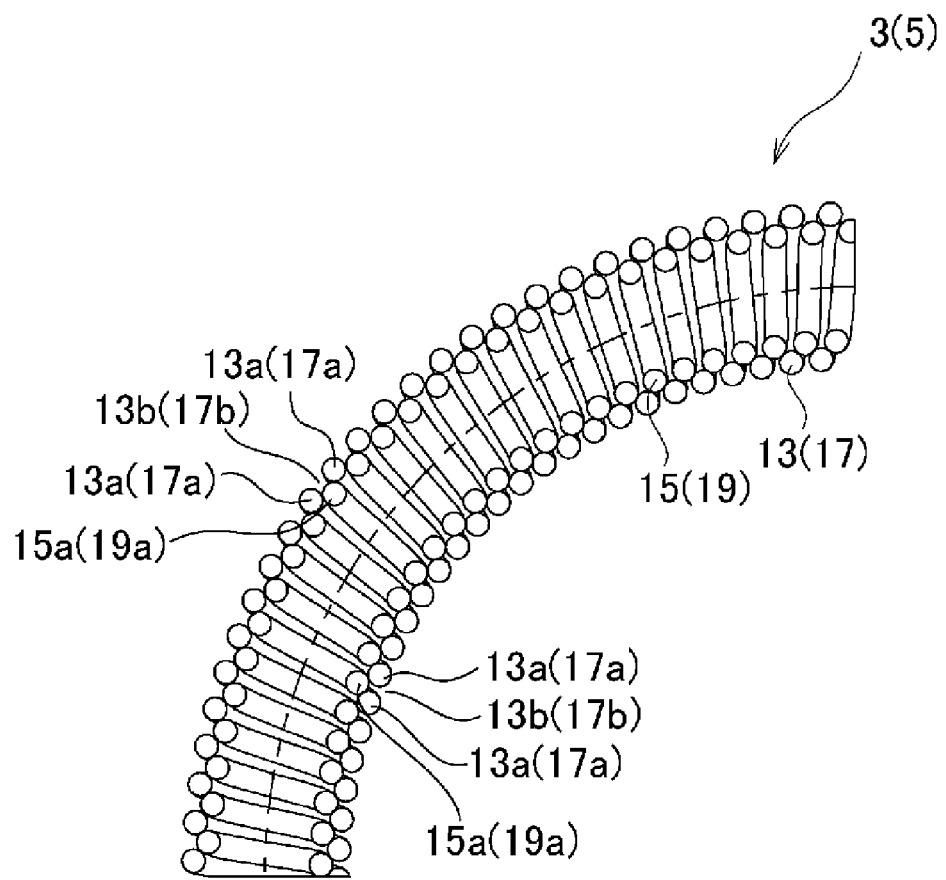
FIG. 5 is a cross-sectional view showing the operation of the inner cylinder.

FIG. 5 is a cross-sectional 1 view showing the inner cylinder 3 when bent. Since the bending of the outer cylinder 5 is the same as the bending of the inner cylinder 3, FIG. 5 may serve as reference. Therefore, reference numerals of the outer cylinder 5 are shown in parentheses in FIG. 5.

When the bending structural body 1 of this example is in a straight state without being bent (when extended), as shown in FIG. 4, the corresponding wound parts 15a of the first inner coil part 15 are fitted between the adjacent wound parts 13a of the first outer coil part 13 of the inner cylinder 3. For the outer cylinder 5, the corresponding wound parts 19a of the second inner coil part 19 are also fitted between the adjacent wound parts 17a of the second outer coil part 17.

Therefore, in the bending structural body 1, even if a compressive force acts in the axial direction, the first inner and outer coil parts 15 and 13 of the inner cylinder 3 and the second inner and outer coil parts 19 and 17 of the outer cylinder 5 are prevented from being compressed, and are prevented from being compressed as a whole. By preventing compression in this way, the posture is stabilized without changing the length of the central part.

Moreover, when the inner cylinder 3 and the outer cylinder 5 are reversely wound, each of the inner cylinder 3 and the outer cylinder 5 is able to resist torsion in the reverse direction. Therefore, even if a torsional force acts, the torsion as a whole is suppressed and the posture is stabilized.

In this way, the bending structural body 1 has high compression resistance and torsion resistance, and is stable in posture, so as to obtain the stable space 21 between the inner cylinder 3 and the outer cylinder 5 and reliably guide the drive wires 9a and the guide wires 9b by the space 21.

The bending structural body 1 may be bent by an operator pulling any one of the drive wires 9a, and is able to be bent 360 degrees in all directions by pulling a combination of different pairs of drive wires 9a. By this bending, an end effector or the like of a manipulator, which is a device to which the bending structural body 1 is applied, may be oriented in a desired direction.

When any one of the drive wires 9a is pulled, as shown in FIG. 5, the pitches 13b and 17b between the adjacent wound parts 13a and 17a of the first and second outer coil parts 13 and 17 of the inner cylinder 3 and the outer cylinder 5 on the inside of the bending become smaller; and the pitches 13b and 17b between the adjacent wound parts 13a and 17a of the first and second outer coil parts 13 and 17 of the inner cylinder 3 and the outer cylinder 5 on the outside of the bending become larger. As a result, the length of the central part of the inner cylinder 3 does not change even when bent, and the posture is stabilized.

At this time, the first and second inner coil parts 15 and 19 of the inner cylinder 3 and the outer cylinder 5 are pushed out toward the outside of the bending. This extrusion of the first and second inner coil parts 15 and 19 is permitted by the enlarged pitches 13b and 17b between the adjacent wound parts 13a and 17a of the first and second outer coil parts 13 and 17 of the inner cylinder 3 and the outer cylinder 5 on the outside of the bending. Therefore, the bending motion is able to be performed smoothly.

Moreover, during bending, the corresponding wound parts 15a and 19a of the first and second inner coil parts 15 and 19 continue to fit between the adjacent wound parts 13a and 17a of the first and second outer coil parts 13 and 17 of the inner cylinder 3 and the outer cylinder 5.

Therefore, as in the straight state, the bending structural body 1 is restrained from being compressed in the axial direction, restrained from fluctuating in the length of the central part from this point, and the posture is stabilized. Therefore, a stable space 21 between the inner cylinder 3 and the outer cylinder 5 is able to be obtained, and the drive wires 9a and the guide wires 9b are reliably guided by the space 21.

Further, when the second inner coil part 19 of the outer cylinder 5 is pushed out, the space 21 between the inner cylinder 3 and the outer cylinder 5 becomes smaller on the inside of the bending, and the space 21 between the inner cylinder 3 and the outer cylinder 5 becomes larger on the outside of the bending.

After bending, both the inner cylinder 3 and the outer cylinder 5 are reliably returned to the uncompressed straight state before bending, in which the first and second inner coil parts 15 and 19 are fitted between the adjacent wound parts 13a and 17a of the first and second outer coil parts 13 and 17. Therefore, the drive wires 9a and the guide wires 9b are reliably guided by the space 21 between the inner cylinder 3 and the outer cylinder 5 in the same manner as before bending.

Effect of Example 1

As described above, this example includes: the inner cylinder 3 which includes the first inner coil part 15 and the first outer coil part 13, and in which corresponding wound parts 15a of the first inner coil part 15 are fitted to the pitches 13b between adjacent wound parts 13a of the first outer coil part 13; the outer cylinder 5 which covers the outer circumference of the inner cylinder 3 with the space 21 and includes the second inner coil part 19 and the second outer coil part 17, and in which the corresponding wound parts 19a of the second inner coil part 19 are fitted to the pitches 17b between adjacent wound parts 17a of the second outer coil part 17; and a plurality of drive wires 9a and guide wires 9b in the circumferential direction which are inserted into and guided by the space 21 between the inner cylinder 3 and the outer cylinder 5 in the axial direction.

Therefore, in this example, by simply arranging the drive wires 9a and the guide wires 9b in the space 21 between the inner cylinder 3 and the outer cylinder 5 that include the inner and outer coil parts 13, 15, 17, 19, it is possible to achieve the bending structural body 1 capable of bending and restoring through an operation of the drive wires 9a with a simple structure.

Moreover, in the bending structural body 1 of this example, compression of the inner cylinder 3 and the outer cylinder 5 are able to be prevented before and after bending. Therefore, the drive wires 9a and the guide wires 9b may be surely guided through the space 21 between the inner cylinder 3 and the outer cylinder 5, and the motion based on the operation of the drive wires 9a is able to be stabilized.

The bending structural body 1 of this example includes the edge members 7a and 7b attached to both ends of the outer cylinder 5 for respectively inserting the drive wires 9a and the guide wires 9b into the first insertion holes 23.

Therefore, the bending structural body 1 is able to position between the drive wires 9a and the guide wires 9b at both ends, and is able to more reliably guide the drive wires 9a and the guide wires 9b.

In addition, the bending structural body 1 of this example includes the flexible tube 11 inserted through the first inner coil part 15 of the inner cylinder 3, and the edge members 7a and 7b have the second insertion holes 25 for inserting the flexible tube 11 in the axial center.

Therefore, in this example, the inside of the first inner coil part 15 of the inner cylinder 3 is able to be used as a path through which the flexible tube 11 is inserted. Moreover, since the inner cylinder 3 is positioned on the edge members 7a and 7b via the flexible tube 11 and the outer cylinder 5 is attached to the edge members 7a and 7b to be positioned, it is possible to reliably position between the inner and outer cylinders 3 and 5 to perform the bending motion smoothly. Moreover, the space 21 between the inner and outer cylinders 3 and 5 is able to be defined accurately to more reliably guide the drive wires 9a and the guide wires 9b.

Further, in this example, when the first inner and outer coil parts 15 and 13 of the inner cylinder 3 and the second inner and outer coil parts 19 and 17 of the outer cylinder 5 are reversely wound to each other, the inner cylinder 3 and the outer cylinder 5 are able to resist torsion in different directions to improve the torsional rigidity as a whole.

Example 2

Figure 6:
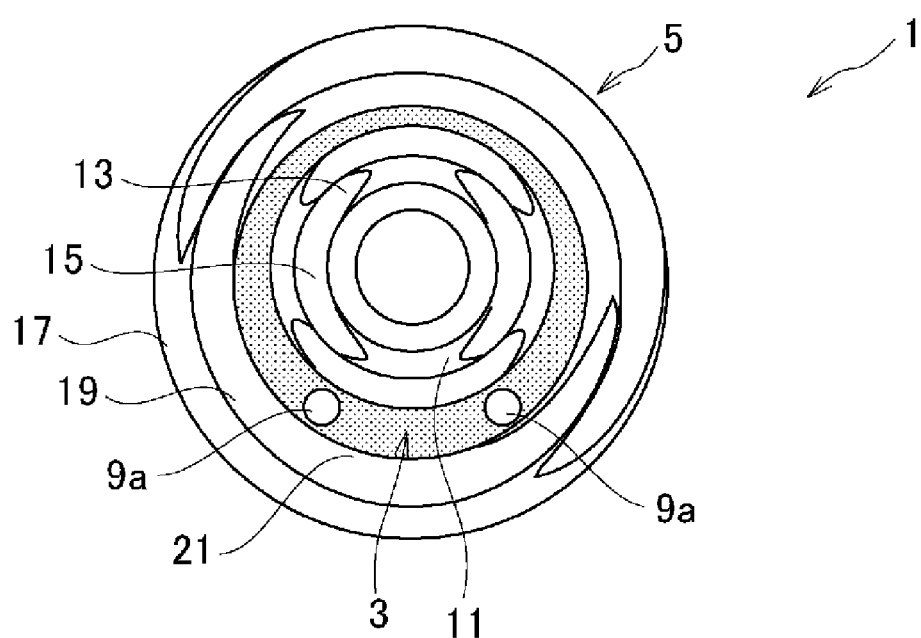
FIG. 6 is a plan view of the bending structural body according to Example 2 of the invention with the edge member omitted.

FIG. 6 is a plan view of the bending structural body according to Example 2 of the invention with the edge member omitted. In addition, in Example 2, the same code is attached to the structure corresponding to Example 1, and the repeated description is omitted.

In Example 2, the centers of the inner cylinder 3 and the outer cylinder 5 are shifted. Others are the same as Example 1.

In this example, by shifting the centers O and O' of the inner cylinder 3 and the outer cylinder 5, the space 21 in one of the shifting directions is narrower than the other. The space 21 in one of the shifting directions is so narrow that the space 21 does not allow the drive wires 9a to be arranged. The drive wires 9a are arranged only in the space 21 on the other side in the shifting direction.

Therefore, in Example 2, by omitting the drive wires 9a, it is possible to reduce the size (reduce the diameter). In addition, even in Example 2, the same effects as in Example 1 may be achieved.

What is claimed is:

1. A bending structural body, comprising:
    an inner cylinder which comprises a first inner coil part and a first outer coil part, and in which wound parts corresponding to the first inner coil part are fitted to spaces between adjacent wound parts of the first outer coil part;
    an outer cylinder which covers at least part of an outer circumference of the inner cylinder with a space therebetween and comprises a second inner coil part and a second outer coil part, and in which wound parts corresponding to the second inner coil part are fitted to spaces between adjacent wound parts of the second outer coil part; and
    wires which are inserted into and guided by the space between the inner cylinder and the outer cylinder in an axial direction; and
    edge members attached to both ends of either one or both of the outer cylinder and the inner cylinder,
    wherein each of the edge members has a first insertion hole penetrated therethrough for inserting the wires.

2. The bending structural body according to claim 1, comprising a flexible member inserted through the first inner coil part of the inner cylinder,
    wherein each of the edge members has a second insertion hole for inserting the flexible member.

3. The bending structural body according to claim 2, wherein the wires comprise a drive wire for driving one of the edge members with respect to another one of the edge members, and a guide wire provided on both sides of the drive wire in a circumferential direction to limit a path of the drive wire.

4. The bending structural body according to claim 2, wherein the first inner and outer coil parts of the inner cylinder and the second inner and outer coil parts of the outer cylinder are reversely wound to each other.

5. The bending structural body according to claim 1, wherein the wires comprise a drive wire for driving one of the edge members with respect to another one of the edge members, and a guide wire provided on both sides of the drive wire in a circumferential direction to limit a path of the drive wire.

6. The bending structural body according to claim 5, wherein the first inner and outer coil parts of the inner cylinder and the second inner and outer coil parts of the outer cylinder are reversely wound to each other.

7. The bending structural body according to claim 5, wherein either one or both of the drive wire and the guide wire are current-carrying paths.

8. The bending structural body according to claim 5, wherein the first inner and outer coil parts of the inner cylinder and the second inner and outer coil parts of the outer cylinder are reversely wound to each other.

9. The bending structural body according to claim 1, wherein the first inner and outer coil parts of the inner cylinder and the second inner and outer coil parts of the outer cylinder are reversely wound to each other.

* * * * *